United States Patent [19]

Hengst et al.

[11] Patent Number: 4,669,819
[45] Date of Patent: Jun. 2, 1987

[54] CONNECTOR FOR COUPLING A MEDICAL LASER TOOL TO A LASER

[75] Inventors: Thomas Hengst, Haar; Andreas Hahn, Sauerlach, both of Fed. Rep. of Germany

[73] Assignee: Messerschmitt-Boelkow-Blohm Gesellschaft mit beschraenkter Haftung, Munich, Fed. Rep. of Germany

[21] Appl. No.: 733,983

[22] Filed: May 13, 1985

[30] Foreign Application Priority Data

Jun. 1, 1984 [DE] Fed. Rep. of Germany ... 8416748[U]

[51] Int. Cl.$^4$ .............................................. G02B 6/24
[52] U.S. Cl. ............................... 350/96.20; 350/96.26
[58] Field of Search ............... 350/96.10, 96.18, 96.20, 350/96.26

[56] References Cited

U.S. PATENT DOCUMENTS 4,170,997 10/1979 Dinnow et al. .............. 350/96.26 X
4,199,222 4/1980 Ikushima et al. .............. 350/96.2 X Primary Examiner—Eugene R. LaRoche
Assistant Examiner—James C. Lee
Attorney, Agent, or Firm—W. G. Fasse; D. H. Kane, Jr.

[57] ABSTRACT

A connector for coupling a medical laser tool to a laser has a housing with a coupling fitting at one end which is plugged into a laser receptacle and with a light conductor cable connection at the other end. The light conductor cable in turn is connected to the laser tool. The coupling fitting includes, in addition to the optical coupling element, heavy and light duty electrical contact members for an electrical power and data transmission and a gas conduit coupling for a gas transmission through the connector.

7 Claims, 2 Drawing Figures

CONNECTOR FOR COUPLING A MEDICAL LASER TOOL TO A LASER

FIELD OF THE INVENTION

The invention relates to a connector for coupling a medical laser tool to a laser. More specifically, the connector includes a light conductor plug-in connector with a sleeve type plug for connection to a receptacle in a laser.

DESCRIPTION OF THE PRIOR ART

In connection with the use of lasers for medical or technical purposes it is necessary to provide a coupling between the laser tool itself and the laser generator which provides the laser beam. In addition to the transmission of the laser beam through a light conductor other conductors are also required for providing an electrical connection as well as a conduit for a gas flow. Heretofore, it has been customary to provide separate coupling elements for the laser beam, for the electrical current, and for the gas flow. Such separate coupling elements resulted in an expensive and frequently involved structure, whereby a handling free of faults of the several coupling elements has not always been assured.

OBJECTS OF THE INVENTION

In view of the above it is the aim of the invention to achieve the following objects singly or in combination:

to construct a connector for coupling a laser tool to a laser, especially a medical laser, whereby the connector is so constructed that it permits the coupling not only of the light conductor, but also simultaneously the coupling of a gas conduit and of a plurality of different types of electrical contacts;

the present coupling connector shall control the closing and opening of the shutter at the laser output;

to control the laser output power in accordance with the power rating of the connected light conductor; and to provide for the data transmission through the coupling connector, for example, for controlling the required gas flow.

SUMMARY OF THE INVENTION

The present connector for coupling a laser tool, especially a medical laser tool to a laser generator is characterized by a connector housing, preferably a cylindrical housing which has a plug-in end for insertion into a respective socket in the laser generator and a cable end for connection to a light conductor cable. The plug-in end houses an optical coupling for transmitting the laser light to the light conductor and such optical coupling is located centrally in the connector so that additional components can be arranged around the centrally located optical coupling. Such additional components are located radially outwardly of the optical coupling and comprise, for example, a coupling for a gas conduit and a plurality of heavy duty electrical contact members, preferably positioned symmetrically relative to the optical coupling members as well as a plurality of further electrical contacts for data transmission purposes arranged in a random fashion relative to each other. Such random arrangement of the further electrical contact prevents an erroneous plug-in. The plug-in end is surrounded by a jacket or sleeve to form a sleeve type plug which fits into a respective socket in the laser generator. If desired, the jacket or sleeve may be provided with locking elements to hold the plug-in end of the connector in the socket against unintended removal.

BRIEF DESCRIPTION OF THE DRAWINGS

The invention will be described below in more detail and by way of example with reference to the accompanying drawings, wherein.

DETAILED DESCRIPTION OF A PREFERRED EXAMPLE EMBODIMENT AND OF THE BEST MODE OF THE INVENTION

Figure 1:
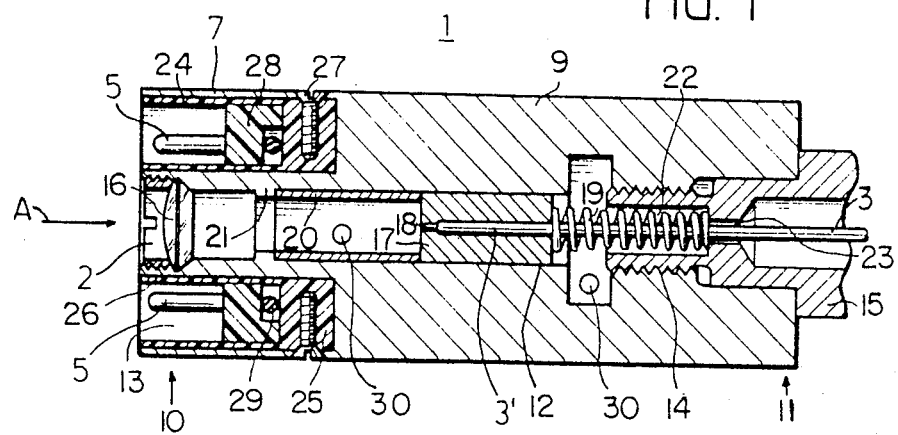
FIG. 1 is a somewhat simplified longitudinal sectional view through a connector according to the invention.

The sectional view of FIG. 1 shows that the connector 1 has a housing 9 with a plug-in end 10 and a cable connector end 11. The housing 9 is provided with a longitudinal through-bore 12 extending entirely through the housing from one end to the other. The plug-in end 10 is provided with a recess 13 surrounded by a sleeve or jacket 7 to form a sleeve type plug which fits into a socket in the housing of the laser not shown. The central through-bore 12 is provided with a threading 14 near the cable end 11 of the housing 9. A connector nipple 15 is threaded into the threading 14 at one end while its other end is conventionally connected to a light conductor cable not shown. A light conductor 3 forming part of such a light conductor cable extends centrally through the nipple 15 and thus centrally through the bore 12. An optical coupling device 16 is held in place in a socket type recess concentric to the central bore 12 by a hollow nut 2. Thus, the optical coupling device 16 is located in the coupling fitting formed inside the jacket 7 around the recess 13. The free end 3' of the light conductor 3 is rigidly connected to a spacer member 17 provided with a light passage 18 and precisely fitting into the bore 12. A spring 19 is inserted between the spacer member 17 and the nipple 15 for pushing the free end 3' of the light conductor 3 into an optically precise position relative to the optical coupling device 16. For this purpose a spacer sleeve 20 is inserted between a shoulder 21 in the through-bore 12 and the spacer member 17. Preferably, the spring 19 is held in place in a cavity 22 in the nipple 15. The light conductor 3 passes freely through a central hole 23 in the nipple 15 and the spring 19 makes sure that the free end 3' of the light conductor 3 is always in the same position relative to the optical coupling device 16.

The recess 13 in the plug-in end of the connector housing 9 is surrounded by the sleeve or jacket 7, the inner wall of which is covered by an electrically insulating lining 24. An insert 25 of electrically insulating material covers the bottom of the recess 13 and has an inner extension 26 of insulating material so that the recess 13 is entirely insulated, except for its open front end. The insert 25 is held in place by screws 27 passing through the sleeve 7. Heavy duty or power transmission electrical contact members 5 are held in place in the recess 13 by an electrically insulating base 28. The contact members 5 are connected to electrical conductors symbolically shown at 29 and leading through the housing 9 in a conventional manner not shown.

Figure 2:
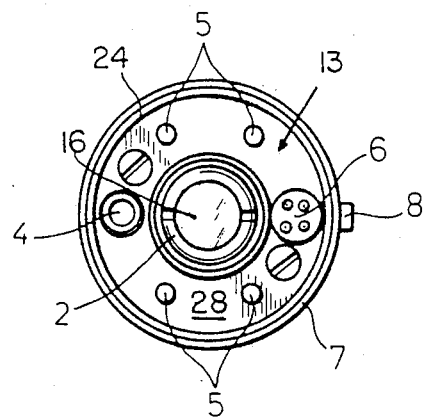
FIG. 2 is a view in the direction of the arrow A in FIG. 1.

Referring to FIG. 2 a gas conduit coupling member 4, for example of the rapid coupling type, is located radially outwardly of the central bore in the recess 13. The power transmission electrical contact members 5 form a first plurality of contacts which are preferably arranged symmetrically relative to the optical coupling device 16. A second plurality of information transmission electrical contact members 6 are located in the recess 13, for example, opposite the gas coupling member 4. The contact members 6 are preferably randomly arranged in such positions that an erroneous plug-in is prevented. The sleeve 7 is, for example, provided with a plug-in locking member 8 of a conventional, bayonet plug-in type.

The gas coupling member 4 leads to openings 3 for rinsing and cooling the light conductor 3 at it's distal end and 3'. The power transmission electrical contact members 5 are used for providing power to relays or to other current users, for example, for closing an optical shutter at the output of the laser generator not shown. Such shutter is, for example, closed when the laser tool, not shown, is disconnected from the other end of the light conductor 3. The information transmitting electrical contacts 6 are used, for example, to transmit data. A group of four such conductors could, for example, be arranged at the corners of a square for avoiding the above mentioned erroneous plug-in. With the aid of the contact 6 it is possible to identify the respective laser tool and to also code the particular type of light conductor. Thus, it is possible to automatically reduce the laser output power with the aid of the contacts 6 in response to the connection of a low power light conductor to the present connector, whereby an overloading of the light conductor is automatically avoided. Furthermore, the contact members 6 can be used for providing instructions to the laser generator and to the other equipment combined with the laser generator. For example, the operator could control the gas flow with the aid of the contacts 6 leading to respective electrically operated valves. Any other technical or physical values relating to the particular type of tool could also be transmitted through the contacts 6.

The special advantage of the invention is seen in that the coupling connector has essentially a single piece housing and a single piece light conductor coupling to that housing in the form of the nipple 15. Simultaneously, other conduits are provided which are arranged in a way to avoid an erroneous connection. The required cooling gas is directly coupled through the laser light conductor connector and the electrical contacts control the shutter of the laser output as well as the power output of the laser light beam and further values needed in connection with the particular laser tool. The respective electrical conductors leading from the tool to the contacts 5 and 6 are not shown but are of conventional construction and may be part of the light conductor cable.

Incidentally, the housing 9 is preferably cylindrical and all the components are arranged concentrically and coaxially relative to the central longitudinal axis of the bore 12.

Although the invention has been described with reference to specific example embodiments, it will be appreciated, that it is intended, to cover all modifications and equivalents within the scope of the appended claims.

What we claim is:

1. A connector for coupling a laser tool to a laser, comprising a connector housing with a central longitudinal through-bore through said housing, a coupling fitting forming a sleeve type plug at one end of said connector housing for connection to said laser, light conductor means including nipple means for connecting a light conductor cable to the other opposite end of said connector housing so that said light conductor extends centrally in said through-bore, optical coupling means arranged in said central through-bore at said one end of said connector housing inside said coupling fitting for transmitting a laser beam into said light conductor, gas conduit coupling means in said fitting for transmitting a gas through said connector, a first plurality of power transmission electrical contact members arranged in said fitting symmetrically relative to said optical coupling means for an electrical power transmission through said connector, and a second plurality of information transmission electrical contact members in said fitting arranged randomly relative to each other for transmitting data information through said connector.

2. The connector of claim 1, wherein said connector housing and said coupling fitting are cylindrical, and wherein said central through-bore extends concentrically through said housing and through said coupling fitting.

3. The connector of claim 1, further comprising locking means (8) for arresting said connector housing in a respective socket in said laser.

4. The connector of claim 1, wherein said connecting means comprise a nipple secured to said light conductor means, said through-bore having an internal threaded section, said nipple having an external threading cooperating with said internal threaded section for securing said light conductor means to said connector housing, a light conductor positioning member rigidly connected to a free end of said light conductor means protruding from said nipple and sized to fit into said through-bore, stop means in said through-bore, and spring means between said positioning member and said nipple for urging said free end of said light conductor means into a defined position relative to said optical coupling means.

5. The connector of claim 4, wherein said stop means comprise a shoulder in said through-bore and a spacer sleeve of defined length between said shoulder and said positioning member for defining the position of said free end of said light conductor means.

6. The connector of claim 4, wherein said nipple has a cavity extending coaxially with said central through-bore, said spring means comprising a helical spring partially received in said cavity, said light conductor means extending through said helical spring.

7. The connector of claim 1, wherein said coupling fitting comprises a substantially cylindrical ring recess in said one end of said connector housing, said ring recess having a recess bottom and inner and outer ring walls, electrical insulating means covering said inner and outer ring walls and said recess bottom, and means securing said electrical insulating means in said ring recess.

* * * * *